US005964093A

United States Patent [19]

Heinemann et al.

[11] Patent Number: 5,964,093

[45] Date of Patent: Oct. 12, 1999

[54] GAS HYDRATE STORAGE RESERVOIR

[75] Inventors: Robert Frederick Heinemann; David Da-Teh Huang; Jinping Long, all of Plano, Tex.; Roland Bernard Saeger, Runnemede, N.J.

[73] Assignee: Mobil Oil Corporation, Fairfax, Va.

[21] Appl. No.: 08/950,249

[22] Filed: Oct. 14, 1997

[51] Int. Cl.[6] ................................ F17C 1/12; F17C 7/00; F17C 13/00; C07C 9/00

[52] U.S. Cl. ............................ 62/45.1; 62/46.1; 62/53.1; 585/15

[58] Field of Search .................................... 62/45.1, 46.1, 62/46.2, 48.1, 53.1; 585/15

[56] References Cited

U.S. PATENT DOCUMENTS

| | | |
|---|---|---|
| 2,270,016 | 1/1942 | Benesh . |
| 2,375,559 | 5/1945 | Hutchinson et al. . |
| 2,904,511 | 9/1959 | Donath . |
| 3,170,870 | 2/1965 | Bachman . |
| 3,514,274 | 5/1970 | Cahn et al. . |
| 3,856,492 | 12/1974 | Klass . |
| 3,888,434 | 6/1975 | Chersky et al. . |
| 3,954,921 | 5/1976 | Yoshida et al. . |
| 3,975,167 | 8/1976 | Nierman . |
| 4,915,176 | 4/1990 | Sugier et al. . |
| 4,920,752 | 5/1990 | Ehrsam . |
| 4,930,319 | 6/1990 | Bee et al. . |
| 5,473,904 | 12/1995 | Guo et al. . |
| 5,536,893 | 7/1996 | Gudmundsson . |
| 5,562,891 | 10/1996 | Spencer et al. . |

FOREIGN PATENT DOCUMENTS

| | | |
|---|---|---|
| WO93/01153 | 1/1993 | WIPO . |

OTHER PUBLICATIONS

W.P. Gee, et al., "The Solvent Dewaxing Process," *Refiner & Natural Gasoline Manufacturer*, vol. 15, No. 16, (1936), pp. 205–209.

B. Miller, et al., "Hydrate Storage of Natural Gas," *American Gas Association Monthly*, vol. 28, No. 2 (1946), pp. 63–67, 92.

D. Katz, et al., *Handbook of Natural Gas Engineering*, McGraw–Hill, New York (1959) pp. 189–221.

H.C. Kim, "Kinetics of Methane Hydrate Decomposition," *Chemical Engineering Science*, vol. 42, No. 7 (1987), pp. 1645–1653.

(List continued on next page.)

*Primary Examiner*—Christopher B. Kilner
*Attorney, Agent, or Firm*—Robert B. Furr, Jr.; Malcolm D. Keen

[57] ABSTRACT

A gas hydrate storage reservoir includes at least one insulated wall defining an opening and a sunlight permeable top covering the opening. A gas-tight, gas hydrate storage cavity is defined within the top and the wall(s). A cover element is provided to cover at least a portion of the top to prevent sunlight from passing through that portion of the top. The gas storage reservoir also includes devices for removing gas and water from the storage cavity. In use, when gas is desired by the user, the cover element is removed from at least a portion of the sunlight permeable top so that sunlight will pass through the top and into the storage reservoir. Heat energy from the sun warms the exposed gas hydrates, thereby forcing the hydrates to dissociate into gas and water. The gas is removed from the tank and transported to an appropriate location for use. When sunlight is unavailable or when additional gas is needed than that produced by dissociation via the sun, an external, auxiliary heater (e.g., one or more heating coils, one or more coils or channels through which steam flows, one or more coils or channels through which a relatively warm gas or liquid flows, one or more electrical heating elements, a steam lance device, or a microwave generator) is provided to heat the hydrates. Through the use of the method and apparatus according to the invention, gas hydrates can be stored and regassified conveniently, inexpensively, and controllably, without loss of valuable gas products.

32 Claims, 3 Drawing Sheets

OTHER PUBLICATIONS

A.A. Trofimuk, et al., "The Dynamics of the Zone of Hydrate Formation and its Effect on the Temperature Regime of the Cryolithozone," *Soviet Geology and Geophysics*, vol. 27, No. 11 (1987), pp. 1–7.

I. Ridley, et al., "Gas Hydrates Keep Energy on Ice," *New Scientist*, No. 1601 (1988), pp. 53–58.

Y.P. Handa, "A Calorimetric Study of Naturally Occurring Gas Hydrates," *Industrial & Engineering Chemistry Research*, vol. 27, No. 5 (1988), pp. 872–874.

L.F. Smirnov, "New Technologies Using Gas Hydrates," *Theoretical Foundations of Chemical Engineering*, vol. 23, No. 6 (1990), pp., 514–526 (Russian language original published at Teor. Osn. Khim. Tekhnol. V23(6), 808–822 (1989).

E.D. Ershov, et al., "Experimental Investigations of the Microstructure of Agglomerate of Ice and Methane Hydrate," *Soviet Engineering Geology*, vol. 3 (1990), pp. 32–37.

E.D. Sloan, Gas Research Institute, Topical Report "The State–of–the–Art of Hydrates as Related to the Natural Gas Industry," GRI–91/0302, 1992.

E.D. Ershov, et al., Experimental Research on Gas Hydrate Decomposition in Frozen Rocks, *Cold Regions Science and Technology*, vol. 20 (1992), pp. 147–156.

P. Englezos, "Clathrate Hydrates," *Industrial & Engineering Chemical Research*, vol. 32 (1993), pp. 1251–1274.

J.S. Gudmundsson, "Storing Natural Gas as Frozen Hydrate," *SPE Production & Facilities*, vol. 9, No. 1 (1994), pp. 69–73.

R.D. Malone, "Gas Hydrate Geology and Geography," International Conference on Natural Gas Hydrates, *Annals of the New York Academy of Sciences*, vol. 715, pp. 225–231.

K.A. Kvenvolden, "Natural Gas Hydrate Occurrence and Issues," International Conference on Natural Gas Hydrates, *Annals of the New York Academy of Sciences*, vol. 715, pp. 232–246.

J.S. Gudmundsson, et al., "Transport of Natural Gas as Frozen Hydrate," *Proceedings of the Fifth International Offshore and Polar Engineering Conference*, vol. I, The Hague, Netherlands, Jun. 1995, pp. 282–288.

"Natural Gas Transport as Hydrates 25% Below Cost of LNG," *Offshore*, Nov., 1995, p. 26.

J. Long, "Gas Hydrate Formation Mechanism and Kinetic Inhibition," Ph.D. Dissertation, 1994, Colorado School of Mines, Golden, Colorado.

MS Peters et al., "Plant Design and Economics for Chemical Engineers", McGraw Hill, 1976, pp. 575–586.

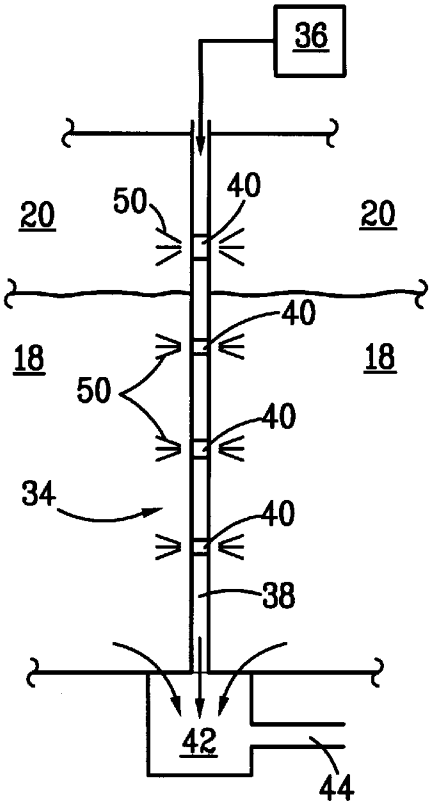
FIG. 4
FIG. 5
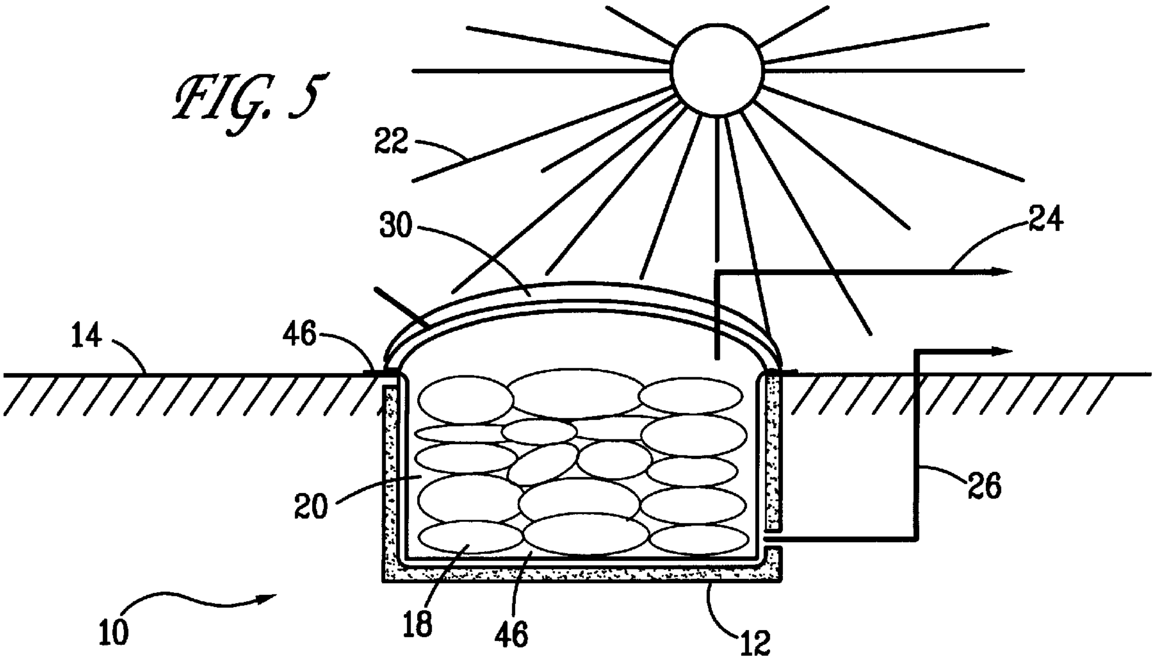

GAS HYDRATE STORAGE RESERVOIR

FIELD OF THE INVENTION

This invention relates to an apparatus and method for storing and regassifying gas hydrates. The invention includes an insulated storage reservoir, preferably located at least partially underground, with a sunlight permeable top to allow the gas hydrates to be exposed to sunlight for regassification. Cover elements are provided to allow controlled exposure of the stored hydrates to sunlight.

BACKGROUND OF THE INVENTION

Gas hydrates have been known for many years. These hydrates are inclusion compounds wherein various light hydrocarbon gases or other gases, such as natural gas, methane, ethane, propane, butane, carbon dioxide, hydrogen sulfide, nitrogen, and combinations thereof, physically react with water at elevated pressures and low temperatures. The gas becomes included or entrapped within the extended solid water lattice network which includes hydrogen bonded water molecules. The hydrate structure is stable due to weak van der Waals' forces between the gas and water molecules and hydrogen bonding between water molecules within the lattice structure.

At least two different hydrate crystalline structures are known, each of which is a clathrate crystalline structure. A clathrate hydrate unit crystal of structure I includes two tetrakaidecahedron cavities and six dodecahedron cavities for every 46 water molecules. A clathrate hydrate unit crystal of structure II contains eight large hexakaidecahedron cavities and 16 dodecahedron cavities for every 136 water molecules. A relatively large volume of gas can be entrapped under pressure in these cavities. For example, it has been determined that natural gas hydrates can contain as much as 180 standard cubic feet of gas per cubic foot of the solid natural gas hydrates.

Early on, gas hydrates were considered an industrial nuisance. Petroleum and natural gas production facilities are often located in cold environments, where the product is located in deep underground or underwater wells. When tapping these wells, all of the necessary ingredients and conditions are present for producing gas hydrates—i.e., light hydrocarbon gases and water are present, the temperature is low, and the pressure is high. Therefore, gas hydrates often would be produced spontaneously in the drilling and transmission pipes and equipment when an oil or natural gas well was tapped. Because gas hydrates are solid materials that do not readily flow in concentrated slurries or in solid form, when they are spontaneously produced in oil or natural gas production, they tend to clog the equipment, pipes, and channels in the production and transmission systems. These disadvantageous properties of gas hydrates spawned much research into methods for inhibiting hydrate formation and eliminating this nuisance. See, for example, D. Katz, et al., *Handbook of Natural Gas,* McGraw-Hill, New York (1959) pp. 189–221; E. D. Sloan, Jr., *Clathrate Hydrates of Natural Gases,* Marcel Dekker, Inc. (1991). These documents are entirely incorporated herein by reference.

But, because of the relatively high volume of gas that potentially can be stored in gas hydrates, eventually researchers began to look at this "nuisance" as a possible method for safely and cost effectively storing and/or transporting gases. See B. Miller, et al., *Am. Gas. Assoc. Mon.* Vol. 28, No. 2 (1946), pg. 63. This document is entirely incorporated herein by reference. Several researchers and patentees have described methods of producing gas hydrates. See, for example, U.S. Pat. No. 3,514,274 to Cahn, et al., which document is entirely incorporated herein by reference.

While there is extensive documentation relating to gas hydrate production processes, less attention is paid in the literature to devices and methods for storing and regassifying the hydrates. These aspects of gas hydrate production also are important. If the gas hydrates cannot be reliably stored for extended time periods, the production thereof is of limited usefulness. Additionally, if the gas hydrates cannot be conveniently and controllably regassified, there is no point to producing and storing the hydrates.

Hutchinson, et al., U.S. Pat. No. 2,375,559 (which patent is entirely incorporated herein by reference), describe a process for hydrating hydrocarbon gases and storing the produced hydrates in storage tanks. Few details are provided in Hutchinson relating to the manner in which these stored hydrates are regassified.

U.S. Pat. No. 2,904,511 to Donath illustrates a water desalination apparatus that produces desalinated water from salt water by forming gas hydrates. Because this patent relates primarily to a desalination method, hydrate storage and gas recovery is not a concern of Donath. Rather, the hydrates are passed immediately into a hydrate decomposition vessel where the gas is liberated from the relatively desalinated water. This Donath patent also is entirely incorporated herein by reference.

Gudmundsson also describes various systems for producing gas hydrates. See, for example, U.S. Pat. No. 5,536,893; WO Patent Publication No. 93/01153; "Transport of Natural Gas as Frozen Hydrate," ISOPE Conference Proceedings, V1, The Hague, Netherlands, June 1995; and "Storing Natural Gas as Frozen Hydrate," SPE Production & Facilities, February 1994. These documents each are entirely incorporated herein by reference. U.S. Pat. No. 5,536,893 describes agglomerating the gas hydrates into solid blocks suitable for long term storage at atmospheric pressure and at a temperature below 0 to −15° C. Few details are provided concerning the method and apparatus used for hydrate storage and regassification.

Gudmundsson discloses storage of gas hydrates under "metastable" conditions, i.e., conditions under which one would normally expect the hydrates to be unstable and decompose. Under these relatively mild metastable conditions (5 to 20° F. and ambient pressure), natural gas hydrates dissociate sufficiently slowly to remain intact for periods of time suitable to ocean transport or large-scale storage (e.g., for 10 days or more). This metastability phenomenon is attributed to spontaneous regassification of the outer surface of a macroscopic hydrate sample. Because the hydrate regassification process is endothermic, once the outer surface of the hydrate sample dissociates, auto-refrigeration freezes the dissociated water to create an ice shell that significantly insulates the bulk hydrates and attenuates the mass transfer rate of gas from within the interior of the sample. This metastability phenomenon allows hydrates to remain stable at relatively mild conditions after they are initially produced.

Traditionally, hydrate-forming gases, such as natural gas, associated natural gas, methane, ethane, propane, butane, carbon dioxide, nitrogen, and hydrogen sulfide, have been stored under high pressures. Liquefied-natural gas and liquefied propane are examples of this type of storage system. Because of the presence of high pressure cylinders, storage of gases under high pressures and liquefied conditions presents a significant safety issue and is very expensive.

SUMMARY OF THE INVENTION

It is an object of this invention to provide a gas hydrate storage reservoir and method that inexpensively, conveniently, and safely stores large-scale accumulations of gas hydrates. Additionally, it is an object of this invention to provide a gas hydrate regassification system and method that allows one to controllably, conveniently, and inexpensively regassify the gas hydrates and remove the gas and water products from the storage reservoir. The invention takes advantage of the favorable properties of gas hydrates and avoids the drawbacks associated with storing gases in a pressurized and/or liquefied condition.

To accomplish these objectives, this invention provides a gas hydrate storage reservoir that includes at least one insulated wall defining an opening and a sunlight permeable top covering the opening. A suitable means is provided for defining a gas-tight, gas hydrate storage cavity within the top and the wall(s). A means for covering at least a portion of the sunlight permeable top is provided to selectively prevent sunlight from passing through that portion of the top. The gas storage reservoir also includes devices for removing gas and water from the storage cavity. In the method of the invention, when gas is desired by the user, a cover element in the means for covering is removed from at least a portion of the sunlight permeable top so that sunlight will pass through the top and into the storage reservoir. Heat energy from the sun warms the exposed gas hydrates, thereby dissociating the hydrates into gas and water components. The gas component is removed from the reservoir and transported to an appropriate location for use.

Sunlight is not always available, however, to regassify the hydrates. For such times (e.g., at night or on cloudy days), the gas hydrate storage reservoir according to the invention further can include a means, optionally located at least partially within the storage cavity, for heating the gas hydrates. This means for heating can take on any suitable form. For example, it may include heating coils, coils or channels through which steam flows, coils or channels through which a relatively warm gas or liquid flows, electrical heating elements, steam lances, or a microwave generator.

The means for covering the sunlight permeable top allows the user to selectively expose some portion of the top to ambient sunlight, to thereby allow sunlight to pass through the top and heat the gas hydrates for regassification. The cover can take on any suitable form, but preferably it is insulated to prevent undesired ambient heat from passing through and heating the hydrates. The means for covering can include one or more cover elements, preferably cover elements that are retractable to expose a succeedingly greater portion of the sunlight permeable top. Advantageously, the means for covering will be able to completely cover the top, completely expose the top, or cover any portion from 0 to 100% of the surface area of the top.

Although the means for covering can be moved manually without departing from the invention, preferably some means is provided for moving the cover element(s) to selectively cover and/or expose at least a portion of the sunlight permeable top. This means for moving can be, for example, any suitable mechanical or electrical device commonly known in the art (e.g., an electric motor).

Through the use of the method and apparatus according to the invention, gas hydrates can be stored and regassified conveniently, inexpensively, controllably, and safely, without loss of valuable gas products.

BRIEF DESCRIPTION OF THE DRAWINGS

The advantageous aspects of the invention will be more fully understood and appreciated when considered in conjunction with the following detailed description and the attached figures, wherein:

FIG. 4 shows a means for heating that can be included in the apparatus of the invention for heating the stored gas hydrates independent of exposure to sunlight; and FIG. 5 shows a simplified schematic diagram of a second embodiment of the apparatus according to the invention from a side view.

DETAILED DESCRIPTION OF THE INVENTION

This invention relates to a storage reservoir for gas hydrates, preferably for large-scale accumulations of gas hydrates. The storage reservoir according to the invention includes at least one insulated wall, preferably located at least partially underground and made from reinforced concrete, with a sunlight permeable top. The top is covered with one or more movable cover elements that will selectively allow sunlight to pass through to the top. In this way, the cover and walls will protect and insulate the stored gas hydrates from the heat of the ambient environment, but when regassification of the hydrates is desired, the cover element(s) can be moved a predetermined amount to allow sunlight to shine on the hydrates. This will heat the hydrates, causing them to dissociate and making the stored gas available to the user.

Any suitable hydrate-forming gas can be used in the method and apparatus according to this invention. Examples of suitable hydrate-forming gases include natural gas, associated natural gas, methane, ethane, propane, butane, carbon dioxide, nitrogen, and hydrogen sulfide, as well as combinations of these gases. The hydrates can be produced by any suitable process known in the art, such as those processes described in the various documents noted above. Additionally, the gas hydrates can be produced by the process described in U.S. patent application Ser. No. 08/950,246, filed Oct. 14, 1997 in the names of inventors Jinping Long, Roland B. Saeger, David D. Huang, and Robert F. Heinemann entitled "Method and Apparatus for Producing Gas Hydrates." This patent application is entirely incorporated herein by reference.

Figure 1:
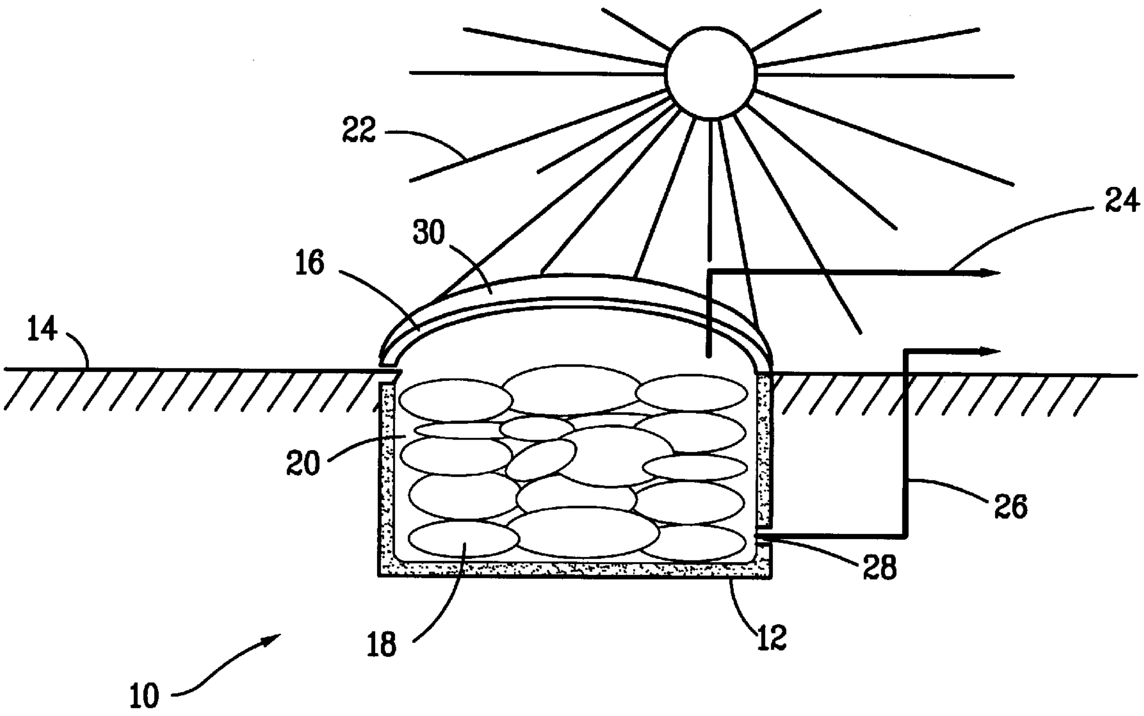
FIG. 1 shows a simplified schematic diagram of a first embodiment of the apparatus according to the invention from a side view.

One embodiment of the storage reservoir 10 according to the invention is schematically illustrated in FIG. 1. Reinforced concrete walls 12 are provided at least partially under the surface of the ground 14. In addition to the insulation provided by being located underground, the walls 12 can be independently insulated using any appropriate type of insulation material (e.g., foam, fiberglass insulation, etc.). A sunlight permeable top 16 covers the walls 12 of the storage reservoir 10. Preferably, the top 16 is made from a clear, double-pane, insulated glass or plastic material. A vacuum, air, or another appropriate gas typically is included in the space between the two panes of glass or plastic in order to provide insulation.

The storage reservoir 10 according to the invention includes at least one wall 12 and the top 16. The storage reservoir 10 can take on any suitable shape including spherical, hemispherical, cylindrical, etc. If cylindrical, the cross-sectional shape of the cylinder can be any shape, such as square, rectangular, circular, oval, elliptical, etc. The embodiment of the invention illustrated in FIGS. 1–3 and 5 is cylindrically shaped with a round cross-section. While FIG. 1 shows the walls 12 located underground, this is not a requirement of the invention. Rather, the invention can be practiced using a free standing, above ground storage reservoir or a partially underground storage reservoir.

The storage reservoir 10 also includes, if necessary, a suitable means for maintaining the stored hydrates at a temperature and pressure suitable for long-term storage. For example, the apparatus according to the invention can maintain the gas hydrates under stable conditions (i.e., conditions suitable for hydrate formation) or metastable conditions (e.g., 0 to −15° C. at ambient pressure, conditions under which one would expect the hydrates to decompose, but where, in fact, they remain stable). The storage reservoir 10 can include refrigeration and pressurization devices known in the art in order to maintain the reservoir 10 at any suitable storage temperature and pressure conditions, without departing from the invention.

In use, gas hydrates 18 are stored in a storage cavity 20 defined in the storage reservoir 10. As sunlight 22 passes through the sunlight permeable top 16, the stored gas hydrates 18 heat up and dissociate into a gas component and a water component. The liberated gas is collected by any suitable means known in the art (e.g., in vents provided in the cavity 20) and removed from the storage cavity 20 via gas line 24. From here, the gas can be transported or stored in any suitable manner for any use. For example, it could be burned to provide heat for a dwelling or an industrial process, it could be pressurized and placed in a tank for further storage and/or transport, etc.

Upon dissociation, the liberated water falls to the bottom of the storage cavity 20 where it can be collected (e.g., in a sump) and removed via a pump. This is illustrated generally by the water removal line 26 in FIG. 1. Alternatively, as long as the liberated water meets all appropriate environmental standards for release, it could simply be allowed to drain from the tank into the surrounding ground.

The gas hydrate storage reservoir 10 also can be made gas-tight by any suitable means known in the art. In the embodiment illustrated in FIG. 1, sealants 28 (such as polymeric or silicone sealants) are provided to seal the junction between the side wall and the bottom wall of the reservoir 10. A gasket arrangement, O-ring, or other suitable sealing means (not shown) can be provided between the sunlight permeable top 16 and the side wall(s) 12 to maintain the cavity 20 in a gas-tight condition.

An appropriate opening is provided, either in a wall 12 or in the sunlight permeable top 16, to allow the storage cavity 20 to be filled with gas hydrates 18. Of course, the opening should be sealable in a gas-tight manner. Alternatively, the top 16 could be completely or partially removable to allow an opening for introducing the hydrates 18. It is advantageous, however, to provide the filling opening in a wall 12, because this will allow a user to add gas hydrates to the storage cavity 20 without opening the top 16 and exposing the gas hydrates 18 present in the storage cavity 20 to sunlight and/or ambient heat.

To prevent unwanted exposure of the stored gas hydrates 18 to sunlight, a suitable cover means is provided to block the sunlight. The cover means is illustrated generally at reference number 30 in FIG. 1. Preferably, this cover means 30 will be insulated or made from an insulative material to prevent unwanted heating of the gas hydrates 18. Any suitable cover means can be used without departing from the invention. For example, the cover means 30 can be located inside or outside the storage cavity 20. Additionally, it can be located immediately adjacent to the top 16, or it can be spaced from the top 16.

Figure 2:
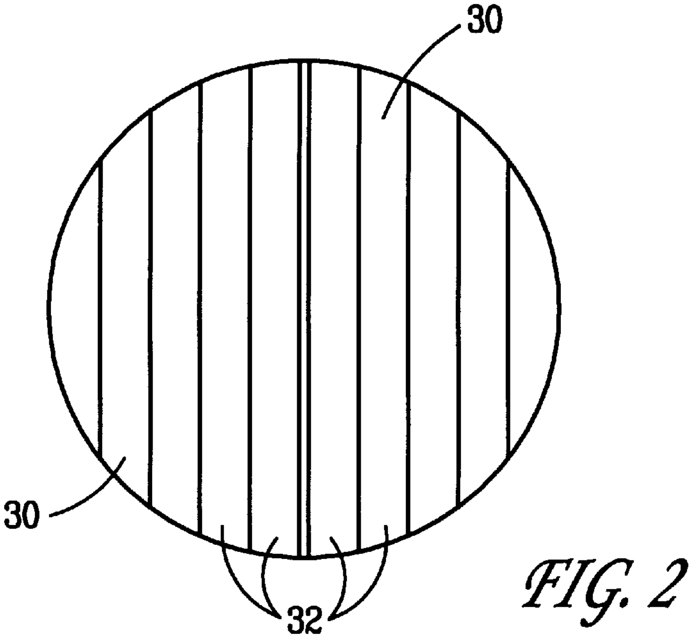
FIG. 2 shows an overhead view of the apparatus according to the invention with the cover elements in place.
Figure 3:
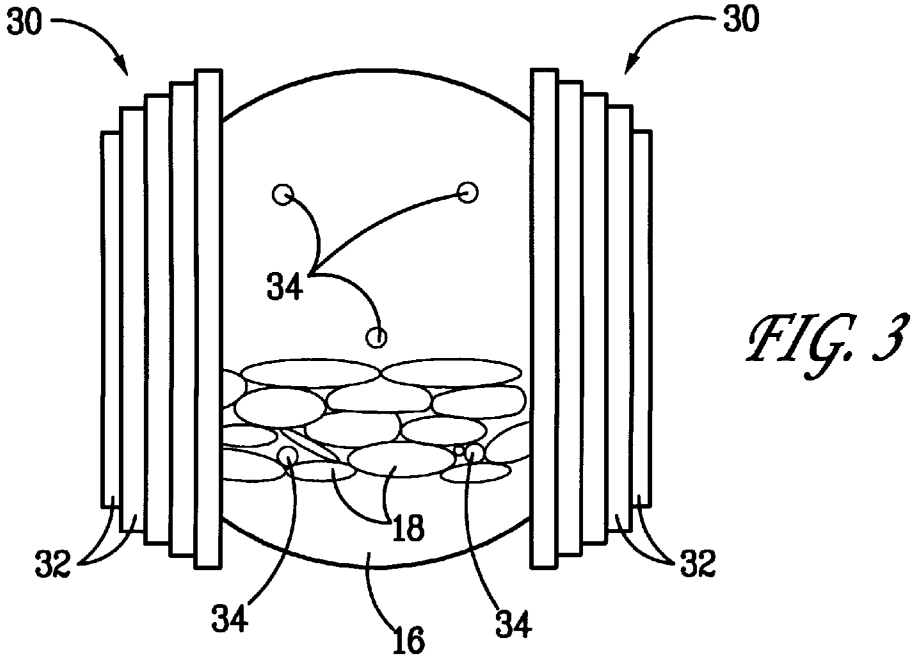
FIG. 3 shows an overhead view of the apparatus according to the invention wherein the cover elements are partially retracted to expose a portion of the sunlight permeable top and storage cavity.

One example of a possible cover means 30 is illustrated in FIGS. 2 and 3. In this instance, the cover means 30 includes a plurality of retractable sunlight opaque shutters or cover elements 32 that can be moved to selectively cover or expose the sunlight permeable top 16. FIG. 2 illustrates a top view when the cover elements 32 are extended over the top 16 to block sunlight from the top 16. In this manner, the cover elements 32 block the sunlight and prevent the gas hydrates 18 within the storage cavity 20 from heating and dissociating. When gas is desired, the cover elements 32 are moved back a predetermined amount (FIG. 3), for a predetermined time period, to expose a predetermined amount of the surface of the sunlight permeable top 16, and hence the stored hydrates 18, to sunlight. The cover elements 32 can be moved any amount so that any portion (0 to 100%) of the surface of the top 16 is exposed to the sunlight, depending on the amount of dissociated gas and the rate of dissociation desired.

The cover elements 32 can be moved in any appropriate manner known in the art. For example, they can be physically moved by a worker at the scene. Alternatively, they can be moved mechanically or electronically using any suitable moving mechanism. Preferably, the cover elements 32 can be activated by an operator using a remote control device.

Other possible cover element configurations are evident to the skilled artisan. Instead of retracting by sliding, as shown in FIGS. 2–3, the individual cover elements 32 could retract by folding up on one another to expose a succeedingly increasing amount of the top 16 to sunlight. As another possible alternative, the cover means 30 could be composed of a single cover element 32 that is removed, retracted, swung, or pivoted to expose the top 16 to sunlight. Also, the cover elements 32 can be rotatably arranged to cover and/or expose the top 16.

The overhead view of FIG. 3 shows another feature of the preferred embodiment of the invention. Sunlight is not always available to heat the gas hydrates, and it does not always provide adequate heat to maintain a desired gas hydrate dissociation rate (i.e., a gas flow volume). Therefore, the storage reservoir 10 according to the invention preferably includes an auxiliary heating means 34. This auxiliary heating means 34 can take on any suitable form. For example, it can include pipes that extend through the storage cavity 20 and into the stored hydrates 18. Heated gas (e.g., steam) or liquid can flow through the pipes, thereby transferring heat through the pipes and into the adjacent hydrates. These pipes can extend straight through the gas hydrates, or they can be coiled around throughout the storage cavity 20.

One suitable auxiliary heating means 34 is the device for producing steam lances shown in more detail in FIG. 4. In this device, steam from a suitable source 36 is forced through pipe 38 under pressure. The pipe 38 extends through the storage cavity 20 where the gas hydrates 18 are located. As it passes through the pipe 38, steam is forced out of suitable openings or nozzles 40 in the pipe and into the surrounding area. The steam forced out of the pipe 38 is said to form a "steam lance," shown as reference number 50 in FIG. 4. Gas hydrates in the area surrounding the openings or nozzles 40 are heated by the heat of the steam lances and are dissociated into gas and water. The liberated gas can be collected for use, and the dissociated water can be removed from the storage cavity 20, as described above.

As desired, the pipe 38 can be insulated for more controlled heating, or it can be formed of a thermally conductive material that will allow heat from the steam to pass through the pipe 38 by conduction and into the stored hydrates 18.

Excess steam and condensed water from within the pipe 38 can be collected, for example, in a sump 42. From there, it can be transported, via line 44, through a recycle loop or to disposal. If desired, the water drained from the storage cavity 20 also can be collected in the sump 42.

Other types of auxiliary heating means 34 also are available, without departing from the invention. The auxiliary heating means 34 can be located within the storage cavity 20, partially within the storage cavity 20, or completely outside the storage cavity 20. As examples, electrical heating elements can be located within the storage cavity 20. Additionally, the heating means 34 can be a microwave generator that heats the hydrates using microwave energy. Suitable regassification devices that also can be used in this invention are described in U.S. patent application Ser. No. 08/950,247, filed Oct. 14, 1997 in the names of inventors Roland B. Saeger, David D. Huang, Jinping Long, and Robert F. Heinemann, entitled "Gas Hydrate Regassification Method and Apparatus Using Steam or Other Heated Gas or Liquid." This patent application is entirely incorporated herein by reference.

An alternative embodiment of the invention is illustrated in FIG. 5. In this embodiment, the storage cavity 20 is made gas-tight by providing a liner 46 made from a gas impermeable material. This liner 46 can take on any suitable form. For example, it can be made from a removable flexible lining material (e.g., a large plastic bag) that lines the side and bottom walls of the storage cavity 20. Alternatively, the liner 46 can be permanently coated or applied directly onto the side and bottom walls of the storage cavity 20. Any suitable gas impermeable coating or lining material can be used without departing from the invention.

In the embodiment illustrated in FIG. 5, the liner 46 replaces the sealants 28 shown in the embodiment of FIG. 1. Of course, both liner 46 and sealants 28 could be used in a storage reservoir 10 without departing from the invention.

In this application, Applicants set forth various theories and mechanisms in an effort to explain how or why the invention works in the manner in which it works. These theories and mechanisms are set forth for information purposes only. Applicants are not to be bound by any physical, chemical, or mechanical theories of operation.

While the invention has been described in terms of various preferred embodiments using specific examples, those skilled in the art will recognize that various changes and modifications can be made without departing from the spirit and scope of the invention, as defined in the appended claims.

We claim:

1. A gas hydrate storage reservoir, comprising:

at least one insulated wall defining an opening;

a sunlight permeable top covering the opening;

means for defining a gas-tight, gas hydrate storage cavity within the top and the at least one wall;

means for covering at least a portion of the sunlight permeable top to prevent sunlight from passing through that portion of the top;

means for removing gas from the storage cavity; and means for removing water from the storage cavity.

2. A gas hydrate storage reservoir according to claim 1, further comprising means for heating, provided at least partially within the storage cavity, to heat at least a portion of the gas hydrates.

3. A gas hydrate storage reservoir according to claim 2, wherein the means for heating the gas hydrates include at least one heating coil.

4. A gas hydrate storage reservoir according to claim 2, wherein the means for heating includes at least one coil or channel through which steam flows.

5. A gas hydrate storage reservoir according to claim 2, wherein the means for heating includes at least one coil or channel through which a gas or liquid flows.

6. A gas hydrate storage reservoir according to claim 2, wherein the means for heating includes one or more electrical heating elements.

7. A gas hydrate storage reservoir according to claim 2, wherein the means for heating includes one or more steam lances.

8. A gas hydrate storage reservoir according to claim 1, further comprising a microwave generator for heating the gas hydrates.

9. A gas hydrate storage reservoir according to claim 1, wherein the means for covering includes at least one cover element.

10. A gas hydrate storage reservoir according to claim 9, wherein at least one cover element is retractable.

11. A gas hydrate storage reservoir according to claim 9, further comprising means for moving at least one cover element to selectively expose at least a portion of the sunlight permeable top.

12. A gas hydrate storage reservoir according to claim 1, wherein the means for covering selectively covers from 0 to 100% of the sunlight permeable top.

13. A gas hydrate storage reservoir according to claim 12, wherein the means for covering includes a means for moving a cover element to selectively cover 0 to 100% of the sunlight permeable top.

14. A gas hydrate storage reservoir according to claim 1, wherein the at least one wall includes a cylindrical side wall and a bottom wall which, along with the sunlight permeable top, define the storage cavity.

15. A gas hydrate storage reservoir according to claim 14, wherein the means for defining a gas-tight, gas hydrate storage cavity includes a gas-tight sealant between the side wall and the bottom wall.

16. A gas hydrate storage reservoir according to claim 1, wherein the at least one wall includes four side walls and a bottom wall which, along with the sunlight permeable top, define the storage cavity.

17. A gas hydrate storage reservoir according to claim 16, wherein the means for defining a gas-tight, gas hydrate storage cavity includes a gas-tight sealant between the side walls and the bottom wall and between adjacent side walls.

18. A gas hydrate storage reservoir according to claim 1, wherein the means for defining a gas-tight, gas hydrate storage cavity includes a polymer material within the cavity.

19. A gas hydrate storage reservoir according to claim 18, wherein the polymer material is a lining provided within the cavity.

20. A gas hydrate storage reservoir according to claim 1, wherein the means for defining a gas-tight, gas hydrate storage cavity includes a sealant material.

21. A gas hydrate storage reservoir according to claim 1, wherein the sunlight permeable top includes glass or plastic.

22. A gas hydrate storage reservoir according to claim 1, wherein the sunlight permeable top includes at least two panes of glass or plastic with an insulating material between the panes.

23. A gas hydrate storage reservoir according to claim 1, further comprising means for heating at least a portion of the gas hydrates.

24. A method for storing and regassifying gas hydrates, comprising:

placing gas hydrates in a storage reservoir including at least one insulated wall defining an opening, a sunlight permeable top covering the opening, and a cover element for covering at least a portion of the sunlight permeable top to prevent sunlight from passing through that portion of the top;

moving at least a portion of the cover element to expose the sunlight permeable top to sunlight;

exposing at least a first portion of the gas hydrates in the storage reservoir to sunlight passing through the sunlight permeable top to regassify the gas hydrates; and collecting gas produced from the gas hydrate regassification.

25. A method according to claim 24, wherein the cover element is moved by a mechanical or electrical device.

26. A method according to claim 24, further comprising heating at least a second portion of the gas hydrates within the storage reservoir using a source of heat other than sunlight.

27. A method according to claim 26, wherein the heating takes place by exposing the second portion of the gas hydrates to at least one heated coil.

28. A method according to claim 26, wherein the heating takes place by passing steam through at least one coil or channel located adjacent to the second portion of the gas hydrates.

29. A method according to claim 26, wherein the heating takes place by passing a gas or liquid through at least one coil or channel located adjacent to the second portion of the gas hydrates.

30. A method according to claim 26, wherein the heating takes place by exposing the second portion of the gas hydrates to heat from one or more electrical heating elements.

31. A method according to claim 26, wherein the heating takes place by exposing the second portion of the gas hydrates to steam from one or more steam lances.

32. A method according to claim 26, wherein the heating takes place by exposing the second portion of the gas hydrates to microwaves.

* * * * *